United States Patent [19]
Rizvi

[11] Patent Number: 5,506,416
[45] Date of Patent: Apr. 9, 1996

[54] MICROSCOPIC INTERNAL REFLECTION INFRARED SPECTROSCOPY TO EXAMINE THE SURFACE OF A TRACE AMOUNT OF MATERIAL

[76] Inventor: Syed A. Rizvi, 3850 Downers Dr., Downers Grove, Ill. 60515

[21] Appl. No.: 249,263

[22] Filed: May 25, 1994

[51] Int. Cl.$^6$ .................... G01N 21/01; G01N 21/17
[52] U.S. Cl. .................... 250/339.06; 250/339.11; 250/341.8; 356/244; 356/440
[58] Field of Search .................... 250/339.12, 339.11, 250/341.1, 341.8, 339.07, 339.08, 339.06; 356/244, 440

[56] References Cited

U.S. PATENT DOCUMENTS

| | | |
|---|---|---|
| 3,415,602 | 12/1968 | Harrick . |
| 3,420,138 | 6/1969 | Hansen . |
| 3,460,893 | 7/1969 | Wilks, Jr. . |
| 4,456,374 | 6/1984 | Langberg . |
| 4,490,618 | 12/1984 | Cielo . |
| 4,732,475 | 3/1988 | Harrick . |
| 4,815,844 | 3/1989 | Schmalfuss et al. . |
| 5,015,092 | 5/1991 | Sting .................... 356/244 X |
| 5,185,640 | 2/1993 | Wilks, Jr. et al. .................... 356/244 X |
| 5,196,901 | 3/1993 | Champetier . |
| 5,216,244 | 6/1993 | Esaki et al. .................... 250/339.11 |
| 5,278,413 | 1/1994 | Yamaguchi et al. .................... 250/339.11 X |

FOREIGN PATENT DOCUMENTS 55-101848  8/1980  Japan .................... 250/341.1
4-116452   4/1992  Japan .

*Primary Examiner*—Carolyn E. Fields
*Assistant Examiner*—Edward J. Glick
*Attorney, Agent, or Firm*—Welsh & Katz, Ltd.

[57] ABSTRACT

A new set of mid-Infrared transparent elements with different geometries to enable examination of the sample surfaces by Internal Reflectance Micro Infrared Spectroscopy is disclosed. The Infrared beam from the IR microscope, either collimated or focused, enters the surface of the element and impinges on an inclined surface of contact between the sample and the element at an angle above the critical angle. This IR beam from the microscope operating in the reflectance mode is then internally reflected at the beveled surface cut at a selected angle, travels inside the IR element, reaches a circular reflector surface where it is reflected back to retrace its initial path. The beam once again comes in contact with the sample at the sample and the element interface and is reflected. The returning of the IR beam to retrace its original path without any significant loss of radiation is accomplished by the following methods: a) the circular end of the outer surface where the internally reflected beam strikes is mirrored from outside b) a retro mirror assembly is placed immediately outside the surface where the internally reflected beam strikes. The center of curvature of this mirror is configured to coincide with the center of curvature of the circular element at the point of contact between the sample and the element.

13 Claims, 5 Drawing Sheets

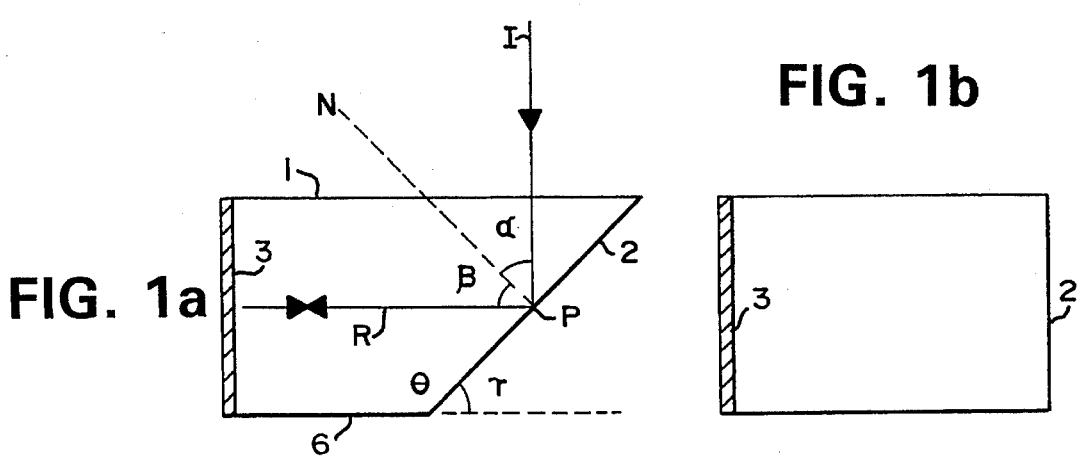
FIG. 1a
FIG. 1b
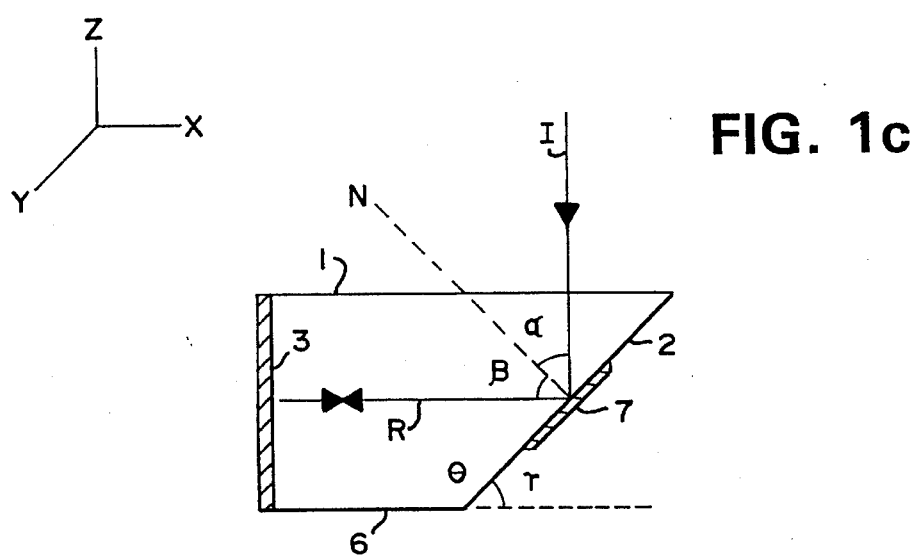
FIG. 1c
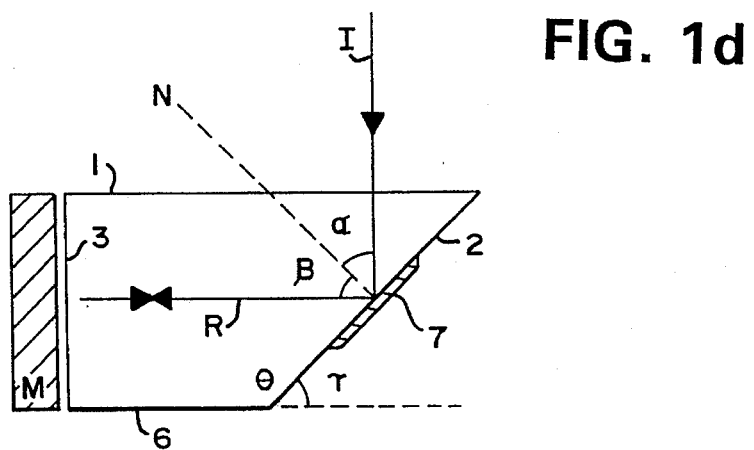
FIG. 1d

MICROSCOPIC INTERNAL REFLECTION INFRARED SPECTROSCOPY TO EXAMINE THE SURFACE OF A TRACE AMOUNT OF MATERIAL

BACKGROUND OF THE INVENTION

This application relates to an apparatus and method for using attenuated total reflectance spectroscopy to analyze surface defects of polymer surfaces.

Internal Reflectance or ATR (Attenuated Total Reflectance) is a widely used Infrared technique for studying materials that provide good optical contact with the beam directing IRE (Internal Reflectance element). Attenuated total reflection utilizes the phenomenon that, under the condition of near total reflection at the interface between a highly refractive transparent medium and the electromagnetic radiation absorbing medium under investigation, such radiation incident on the reflecting interface actually enters the absorbing medium. The reflected radiation is attenuated by this minute penetration and provides a spectrum having absorption bands characteristic of the absorbing medium under investigation. Thus the interaction of the light beam (infrared) with the sample surface at the interface of the sample and the element provides spectral information about the sample. The depth of penetration of the IR radiation into the sample surface can be controlled by varying the angle of incidence of the beam striking the sample-IRE interface. The depth of penetration is also dependent upon the wavelength of radiation and refractive indices of the element (IRE) and the sample, and is defined according to equation 1.

$$D_p = \frac{\lambda_1}{2\pi[\sin^2\alpha - (n_2/n_1)^2]^{1/2}} \quad \text{EQ 1}$$

where $D_p$ = depth of penetration $\lambda_1$ = wavelength of radiation $n_2$ = refractive index of sample $n_1$ = refractive index of the element $\alpha$ = angle of incidence There has been a phenomenal growth in IR microspectroscopy as applied to material sciences in past decade or more. There is a great potential for future growth. Early limitations of micro-transmission and micro-reflectance appear to have been overcome by the introduction of internal reflectance IR micro-spectroscopy. Now samples can be characterized by acquiring spectral data representative of only a few microns from the surface of trace areas. A set of new IR directing elements have been developed which not only allow sampling of the trace surface selectively but at the same time allow the user to control the depth (depth profiling) to which the IR radiation samples the material. This is accomplished by changing selected parameters of equation 1. Depth profiling has become a valuable tool in studying surface defects of certain materials. Specifically, the surface defects of bloomed materials, gel particles, smudges and different types and shapes of domains characteristic of synthetic polymers can now be better analyzed. Opaque samples such as small particles, single fibers, biological samples, tissue samples and forensic samples can be easily characterized which are otherwise difficult to analyze by microtransmission or micro-reflectance IR spectroscopy.

SUMMARY OF THE INVENTION

Therefore, an object of the subject invention is the focal analysis of the surfaces of transparent films and opaque particles.

A further object of the invention is spectral analysis of transparent or opaque surfaces by depth profiling.

There are other objects of the subject application attained by an apparatus and method which uses two different configurations of IR transparent elements, one for focused and the other for a collimated beam. The element for a focused beam can be semicircular with a beveled surface at an inclination of 30 to 60 degrees. The element for a collimated beam entering the surface at 90 degrees is a flat surface element with the beveled surface adjacent to the flat surface and is inclined at 30 to 60 degrees. In either case the element is of a transparent material, preferably of Thallium Bromoiodide (KRS-5), Zinc Selenide, Germanium or other like transparent materials in the spectral region of interest.

A polished metallic sample holder holds the sample for optical as well as IR examination. The wedges of the element and the sample holder are matched when facing each other and are positioned such that when pressed against each other form a substantially continuous contact. IR examination of the sample is accomplished by placing the sample between the sample holder beveled surface and the element beveled surface. The IR beam is then allowed to strike at the point of contact between the sample and the element. The surface that the internally reflected beam strikes is mirrored which enforces the beam impinging upon it to rebound. An alternate set up is possible whereby the internally reflected beam leaves the element and strikes an outside retrofitted mirror having the center of curvature coincidental with the sample-element interface. The beam is reflected back to retrace its incident path. The retrofitted mirror is capable of directional adjustments in the X, Y and Z plane for fine tuning. The element is mounted on a travel guide to facilitate movement in the x-y-z directory, similarly the position of the sample holder can be moved in the x, y and z directions for optical examinations. Once the sample area for the IR analysis is selected, then the position of the sample holder remains fixed during the data acquisition mode.

BRIEF DESCRIPTION OF THE DRAWINGS

Several forms of the novel apparatus of the subject invention will now be described in greater detail with reference to the annexed drawings in which:

FIG. 1A is a side view of an IRE used with the subject invention.

FIG. 1B is a top view of an IRE used with the subject invention.

FIG. 1C is a side view of an IRE with sample used with the subject invention.

FIG. 1D is a side view of an alternative IRE showing sample and the mirror used with the subject invention.

FIG. 2B is a top view of the IRE of FIG. 2a.

DETAILED DESCRIPTION OF THE DRAWINGS

FIGS. 1A, B and C are the drawings of an Internal Reflectance Element (IRE) 1 showing the side, top and side with sample film views respectively, in contact with the IRE. FIG. 1D is essentially the same as that of FIG. 1C with the exception that surface 3 in FIG. 1C is mirrored, whereas FIG. 1D incorporates a flat mirror M that is placed parallel to surface 3. Angle α, β and γ are equal.

Figure 2A:
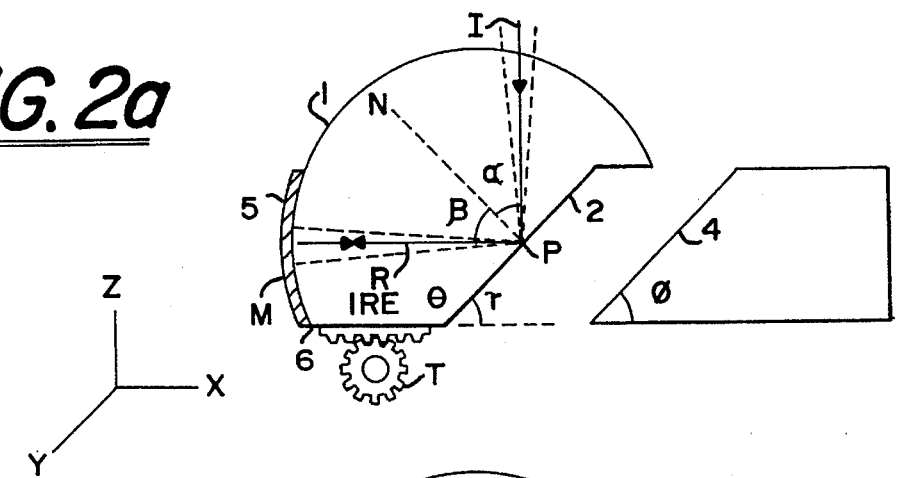
FIG. 2A is a side view of an alternative IRE used with the subject invention.

FIGS. 2A, B and C are the drawings of an IRE similar to that of FIG. 1 with the exception that exterior surface 1 is a curved surface with the center of curvature at the mid-point of surface 2. A metal sample holder with polished surface 4 allows optical and spectroscopic examination of the sample 7 and the area of interest. Angle α, β, and γ are identical. The sample holder beveled surface 4, when positioned as shown in FIG. 2A makes a continuous contact along surface 2. The IRE may be pivoted in the x-z plane to change angle γ by an appropriate mechanism T and the angle of the incident beam is adjusted to maintain the equality of angles α, β and γ. Further the IRE 1 may be pivotable by an appropriate mechanism in the z plane.

Figure 2B:
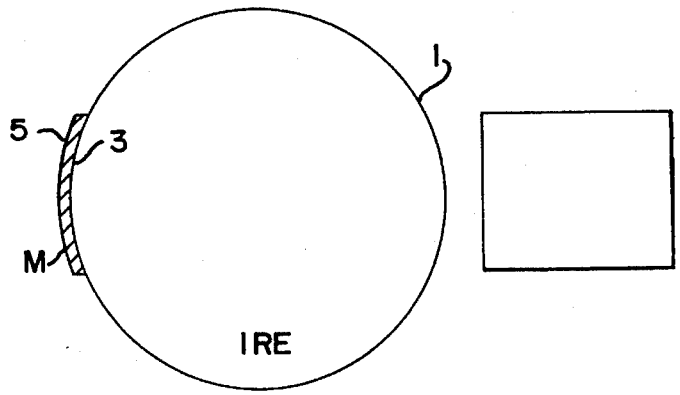
Figure 2C:
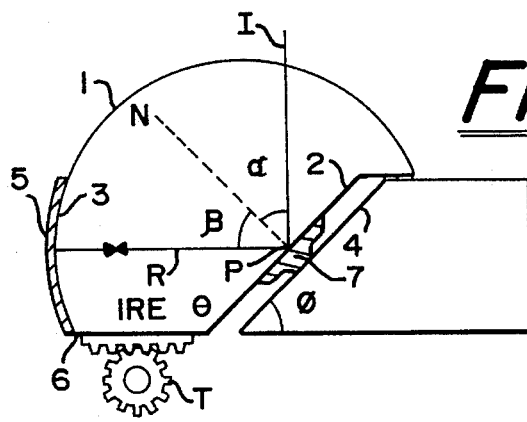
FIG. 2C is a side view of the IRE of FIG. 2a with sample.
Figure 3:
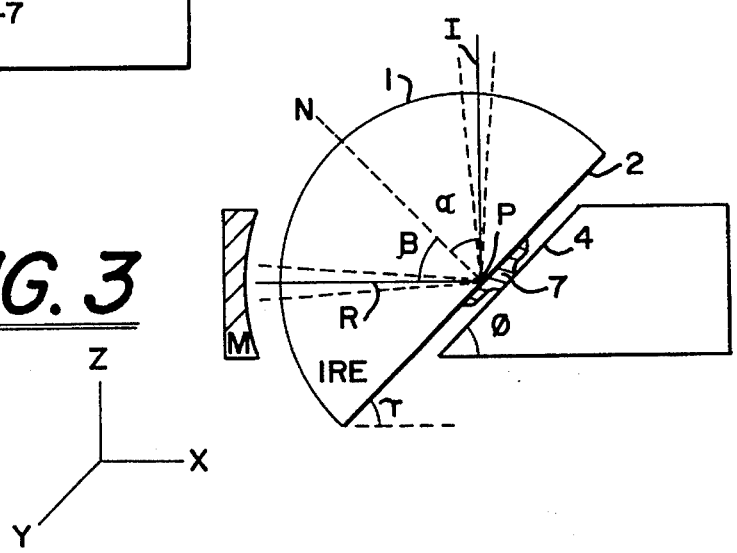
FIG. 3 is a side view of an a hemispherical IRE with sample holder and mirror

An alternative IRE can be utilized according to the subject invention which is similar to that of FIG. 2 with the exception that surface 1 is not a mirrored surface, but instead a circular retro mirror M, capable of adjustments in the x-y-z planes, which is placed immediately outside of surface 1 similar to FIG. 3.

Also with the scope of the subject invention is a hemispherical IRE as in FIG. 3 with a circular outer surface 1 having the center of curvature at a point P along the side 2. Further the hemispherical IRE may have flattened sides or edges (not shown). The external mirror M has a center of curvature that is coincidental with the center of curvature of the IRE at the point of contact between the IRE and the sample and also at the point of ingress/egress of the light beam to and from the mirror M along surface 2. Such identical curvatures minimizes the loss of radiation of the beam being reflected from the external mirror is to M. The purpose of this external mirror is to focus and return the beam striking it to retrace its incident path.

As stated, the subject invention includes an Internal Reflectance Element which allows the examination of trace amounts of sample surface spectroscopically at selected angles of incidence at the IRE-sample interface. These elements can be fabricated from any of the available transparent materials having different indices of refraction in the spectral region of interest. This added flexibility in the choice of IRE materials combined with the ability to change the angle of incidence gives control over the depth of penetration of the radiation into the trace sample surface.

The size of the IRE used is not critical. An element which can be placed on the microscope stage and examined through the microscope is required. Most of the IREs now available are small enough to be placed on the stage of an IR microscope. The size of the sample holder is variable and is dependent on the size of the IRE. Thus, the sample can be optically as well as spectroscopically examined not only in the IR but also in other regions.

The principle of internal reflectance is utilized in acquiring spectral information on a surface of a very small sample size. FIG. 1A is the drawing of a very simple IRE. Surface 1 and 6 are parallel to each other with surface 6 lying in the x-y plane. Surface 3 is a flat mirrored surface lying in the y-z plane. Surface 2 is the beveled surface which makes an angle γ with the x-y plane. The IRE is placed on the IR microscope stage (not shown) and the IR beam I from the IR microscope is positioned to strike surface 1 at an angle, here 90 degrees, in an area defined by the projection of surface 2 on surface 1. This incident beam I enters the IRE and impinges the surface 2 at an angle α to the normal N at some point P. N is the line perpendicular to the surface 2 at P. This beam is then internally reflected at an angle and travels along the path R, strikes the mirrored surface 3 placed outside of the element and is reflected back by the mirrored surface 3 along path R towards the beveled surface 2 and then directed towards the entry point on surface 1 thereby retracing the incident path towards the microscope objective and eventually towards a series of mirrors to an Infrared detector. For purposes of the subject invention the IR Beam I is aimed at point P and the mirrored surface is positioned or formed so that angle α=angle β=angle γ. A sample with good optical contact with surface 2 as shown in FIG. 1C can be then examined by IR. The IR microscope is operated in the reflectance mode. By ratioing the spectra of the IRE with and without the sample, the spectrum of the sample may be generated. FIG. 1D is the side view of a similar IRE where the mirrored surface 3 is substituted by a flat mirror M capable of adjustments in the x-y-z plane which is placed immediately outside as shown. Although the IRE shown in FIG. 1 allows examination of the sample, with this set-up the sensitivity is low, but can be significantly improved by changing the geometry of the IRE. Even with a collimated beam there is a certain degree of beam spread when the beam strikes surface 2. A further loss in energy is observed when the internally reflected beam R is reflected backwards by the mirrored surface 3.

FIG. 2A is a modified version of the IRE described previously. The difference between the two designs is with respect to surface 1. Surface 1 is a curved surface with the center of curvature at a point P on the surface 2. A second modification involves addition of a sample holder with a beveled surface having an angle φ. This sample holder surface 4 as shown in FIG. 2 is polished. The position of the beveled surface 4 of the sample holder and the beveled surface 2 of the IRE is shown in FIG. 2. Angle α of the sample holder and angle γ of the IRE are identical. Further, angle α=angle β=angle φ. See FIGS. 2A and C. The sample holder and the IRE are mounted on rails. The sample holder maintains a fixed position during data acquisition mode but the IRE can be moved backwards and forwards in the x direction by an appropriate mechanism as known in the art. A sample under examination is placed on the polished surface 4 of the sample holder. The sample can be examined optically prior to acquiring IR data on a selected area. The IRE is then moved in the forward direction to come in contact with the sample as shown in FIG. 2C. The curved mirrored surface 5 returns the internally reflected beam at point P to retrace its incident path. In addition to that shown in FIG. 2A a circular retro mirror M placed immediately outside surface 1 as in FIG. 3 and mounted on the same rails that carry the IRE and the sample holder may be used.

FIG. 3 represents an IRE that is specially designed to allow the IR beam to strike the sample-IRE interface at 45 degrees. Angle γ and angle φ are 45 degrees. Angle α is 45 degrees. Again angle γ=angle α=angle β=angle φ.

The capability of x-y-z movement of the circular mirror M with a center of curvature coincident with point P facilitates the focusing of the reflected beam from mirror M along any point on surface 2. This design of the IRE gives the flexibility to change the angle of incidence and hence the depth of penetration of the incident beam into the sample by rotating the IRE in a way that allows an increase or decrease in angle γ hence a corresponding change in angle α. Angle α and Angle φ of the sample holder should be similar. The spectra obtained under these conditions are reasonably good because most of the internally reflected beam is returned by the circular mirror M.

Figure 4:
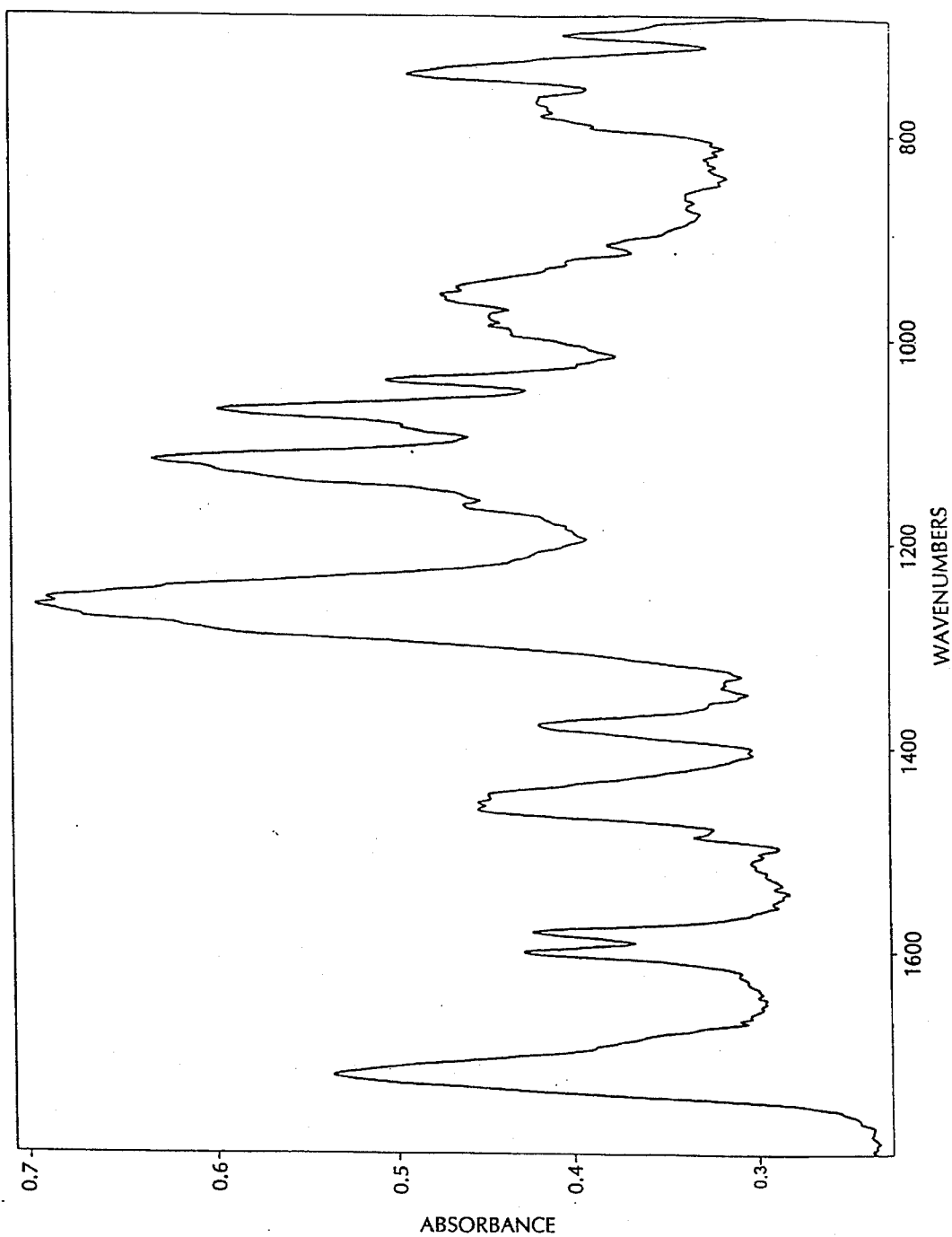
FIG. 4, 5 and 6 are IR spectra obtained from samples using the apparatus of FIG. 1D.
Figure 5:
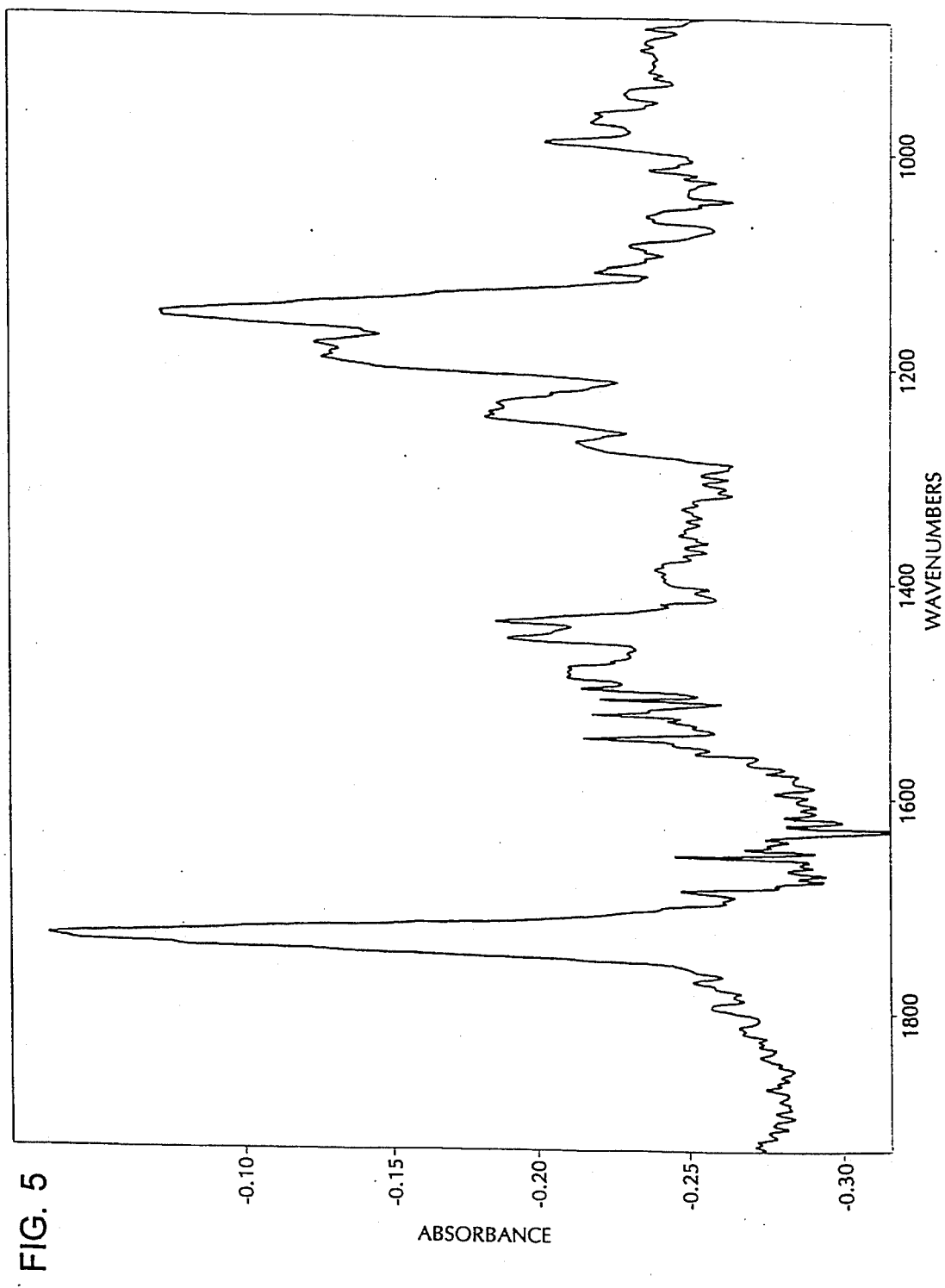
Figure 6:
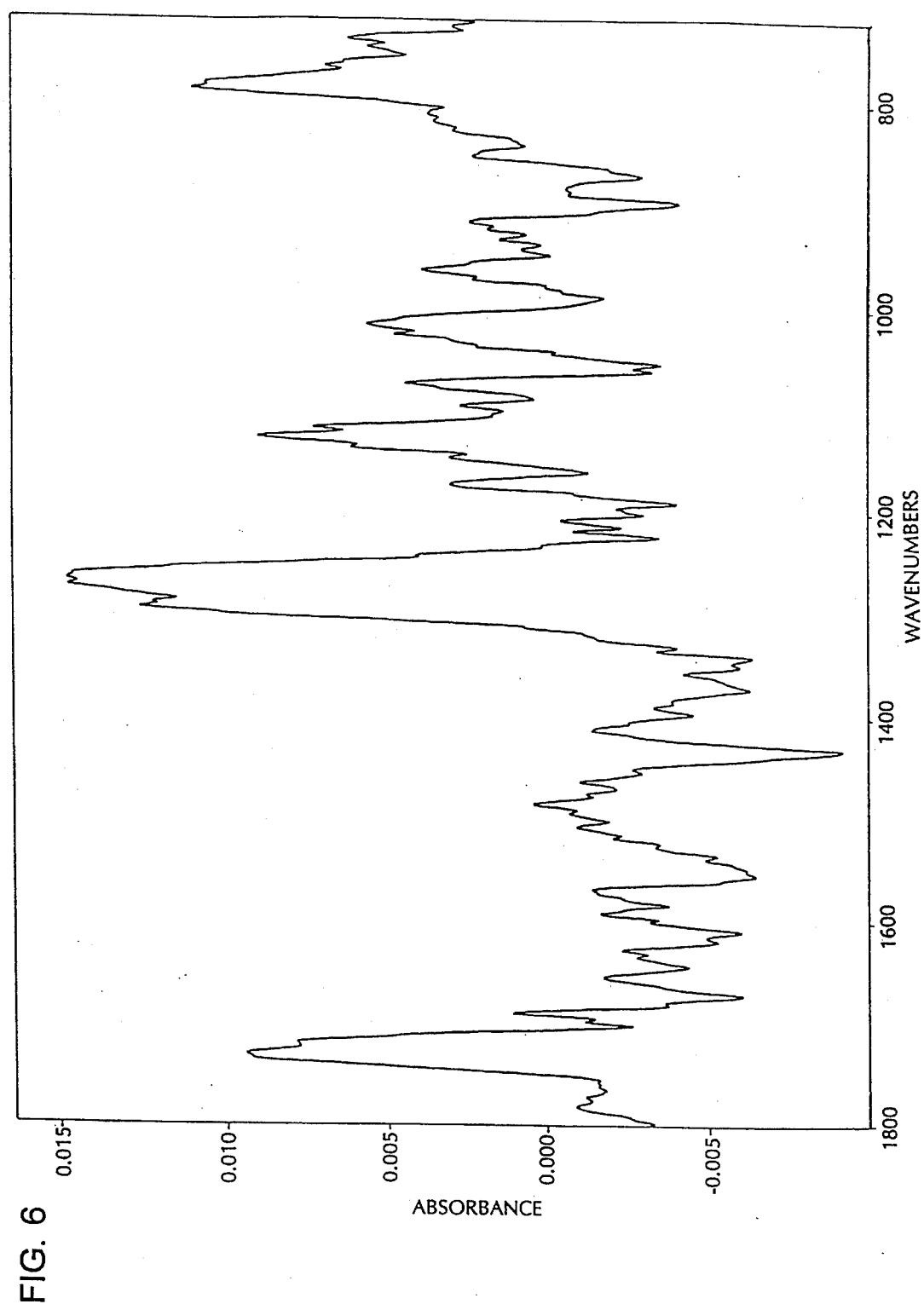

FIGS. 4, 5 and 6 are IR spectra acquired using the IRE shown in FIG. 1D. The IRE and the mirror assembly is placed on the IR microscope stage. The IR microscope used is a SpectraTech IR plan research grade microscope tandem to a Mattson Fourier Transform Infrared Spectrometer. The IREs are 10×5×1 mm with a beveled surface 2 making an angle of 45 degrees with respect to the x-y plane as it sits on the microscope stage. The IR beam emerging through the cassegranian objective is focused at a point along surface 2 at the IRE-sample interface. In this case a sample film of Diethylhexyl phthalate of an area of about 400 um square is casted on surface 2 of the ZnSe IRE as shown in FIG. 2D. A sample film of polymethymethacrylate of an area of about 400 um square is cast on surface 2 of a KRS-5 IRE as shown in FIG. 1D. By masking and aperturing the sample film area exposed to IR radiation from the microscope, this area can be reduced to an area about 80×160 um. Sample IR data is collected and processed. The resulting spectra are displayed in FIGS. 4, 5 and 6 respectively.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments and equivalents falling within the scope of the appended claims.

Various features of the invention are set forth in the following claims.

What is claimed:

1. An internal reflection element for use in internal reflection spectroscopy, comprising:

a transparent element;

a sample holder;

said transparent element having a beveled internal reflection surface at a first angle with respect to the x-y plane;

said sample holder for maintaining a sample in a position for optical analysis on a beveled surface, said beveled surface being at a second angle equal to said first angle;

a mirrored surface spaced from said beveled surface and positioned at a third angle relative to said beveled surface;

said beveled surface having an internally reflecting surface;

such that an incident light beam from a source can enter said internal reflection element at an entry point and travel along a path, strike said internal reflection surface at a point P, be directed to strike said mirrored surface at a point P1, be reflected to retrace said path back through said transparent element to be reflected at point P on said internal reflection surface towards a detector means for analysis.

2. The Internal Reflection Element of claim 1 wherein a line drawn perpendicular to said reflection surface at said point P creates fourth and fifth angles with said incident light beam and said reflected light beam respectively and said first, fourth and fifth angles are equal.

3. The internal reflection element of claim 1 wherein said mirrored surface is external of said transparent optical element.

4. The internal reflection element of claim 3 wherein said mirrored surface is movable in the x, y, and z planes to compensate for the path of said incident light beam.

5. The internal reflection element of claim 1 wherein said transparent optical element is movable in the x, y, and z planes.

6. The internal reflection element of claim 1 wherein said transparent optical element is hemispherical.

7. The internal reflection element of claim 6 wherein said mirrored surface and said transparent optical element have substantially identical centers of curvature.

8. The Internal Reflection Element of claim 1 wherein a line drawn perpendicular to said reflection surface at said point P creates fourth and fifth angles with said incident light beam and said reflected light beam respectively and said second, fourth and fifth angles are equal.

9. A method of spectroscopically analyzing a sample surface comprising the steps of: directing a source of infrared light so that a light beam is reflected from an internally reflective element/sample interface to an adjustable mirrored surface along a light path, positioning said adjustable mirrored surface and said internally reflective element/sample interface relative to each other, and adjusting the position said adjustable mirrored surface to aim said reflected light beam so as to cause said reflected light beam to retrace said light path to said internally reflected element/sample interface and back towards a detector for analysis.

10. The method of claim 9 further including the step of adjusting the position of said IRE/sample interface.

11. An internal reflection element for use in internal reflection spectroscopy, comprising:

a transparent element;

a sample holder;

said transparent element having a spherical exterior surface and a beveled internal reflection surface at a first angle with respect to the x-y plane, said sample holder forming a second angle equal to said first angle, said element being pivotable to change said first angle to a desired angle;

said sample holder for maintaining a sample in a position for optical analysis on a beveled IRE/sample interface, said beveled IRE/sample interface being at an angle equivalent to said second angle;

a mirrored surface space from said beveled IRE/sample interface and positioned at a third angle relative to said beveled IRE/sample interface;

said beveled IRE/sample interface having an internally reflecting surface;

whereby an incident light beam from a source can enter said internal reflection element along a path, strike said internal reflection surface at a point P, be directed to strike said mirrored surface at a point P1, be reflected to retrace said path back through said transparent element to be reflected at point P on said internal reflection surface towards a detector means for analysis.

12. The internal reflection element of claim 11 wherein said mirrored surface is external of said transparent optical element.

13. The internal reflection element of claim 12, wherein said mirrored surface is movable in the x, y, and z planes to compensate for the path of said incident light beam.

* * * * *